US011311644B2

(12) United States Patent
Montenegro et al.

(10) Patent No.: US 11,311,644 B2
(45) Date of Patent: Apr. 26, 2022

(54) ANTIMICROBIAL AND/OR EPITHELIAL CELL GROWTH STIMULATING SUBSTANCE AND COMPOSITION AND TISSUE DRESSING MATERIAL

(71) Applicants: Rivelino Montenegro, Mainz (DE); Thomas Freier, Mainz (DE); Karsten Henco, Dusseldorf (DE)

(72) Inventors: Rivelino Montenegro, Mainz (DE); Thomas Freier, Mainz (DE); Karsten Henco, Dusseldorf (DE)

(73) Assignee: Medoderm GmbH, Mainz (DE)

( * ) Notice: Subject to any disclaimer, the term of this patent is extended or adjusted under 35 U.S.C. 154(b) by 0 days.

(21) Appl. No.: 16/458,915

(22) Filed: Jul. 1, 2019

(65) Prior Publication Data

US 2019/0321511 A1 Oct. 24, 2019

Related U.S. Application Data

(63) Continuation of application No. 13/392,673, filed as application No. PCT/EP2010/062823 on Sep. 1, 2010, now abandoned.

(51) Int. Cl.
*A61L 26/00* (2006.01)
*A61L 15/28* (2006.01)

(52) U.S. Cl.
CPC ........... *A61L 26/0023* (2013.01); *A61L 15/28* (2013.01); *A61L 26/0066* (2013.01); *A61L 2300/232* (2013.01); *A61L 2300/404* (2013.01)

(58) Field of Classification Search
CPC .................. A61K 31/722; A61L 26/0023
See application file for complete search history.

(56) References Cited

U.S. PATENT DOCUMENTS

| | | | |
|---|---|---|---|
| 4,532,134 A * | 7/1985 | Malette | A61K 31/715 514/55 |
| 4,572,906 A | 2/1986 | Sparkes et al. | |
| 2003/0022573 A1 | 1/2003 | Cintio et al. | |
| 2005/0042265 A1 | 2/2005 | Guillot et al. | |
| 2009/0117213 A1 | 5/2009 | Beaulieu et al. | |

FOREIGN PATENT DOCUMENTS

| WO | WO-2008072230 A1 | 6/2008 |
|---|---|---|
| WO | WO-2009028965 A1 | 3/2009 |

OTHER PUBLICATIONS

Chatelet et al., Biomaterials, 2001, 22, p. 261-268. (Year: 2001).*
Azad et al., J Biomed Mater Res Part B: Appl Biomater, 2004, 69B, p. 216-222. (Year: 2004).*
Mattioli-Belmonte et al., Journal of Bioactive and Compatible Polymers, 2007, 22(5), p. 525-538. (Year: 2007).*
Sekar et al., Indian J Dermatol Venereol Leprol, 2008, 74, p. 391-392, Available from: http://www.ijdvl.com/text.asp?2008/74/4/391/42914. (Year: 2008).*
Malmquist et al., J. Oral Maxillofac. Surg., 2008, 66, p. 1177-1183. (Year: 2008).*
Reddi, B.AJ., Int. J. Med. Sci. 2013, 10(6), p. 747-750. (Year: 2013).*
European Patent Office, International Search Report and Written Opinion of the International Search Authority for Corresponding International Patent Application PCT/EP10/062823 dated Jan. 14, 2011 (11 pages).
Minagawa, Tatsuya et al., "Effects of molecular weight and deacetylation degree of chitin/chitosan on would healing", 2007 Carbohydrate Polymers 67 (pp. 640-644).

* cited by examiner

*Primary Examiner* — Jonathan S Lau
(74) *Attorney, Agent, or Firm* — Harris Beach PLLC; Laura W. Smalley

(57) ABSTRACT

A chitosan for use in an antimicrobial treatment of a patient's tissue and a pharmaceutical composition comprising a chitosan for use in an antimicrobial treatment of a patient's tissue. A method of treating a microbial infection, the method comprising the step of administering to a patient an effective amount of a chitosan and an aqueous solution comprising chitosan. A chitosan or a pharmaceutical composition comprising a chitosan for use in an epithelial cell growth stimulating treatment of a patient's tissue. A method of stimulating the growth of epithelial cells the method comprising the step of administering to a patient or to an epithelial cells containing cell culture an effective amount of a chitosan or a pharmaceutical composition comprising chitosan. A tissue dressing material characterized in that it consists of chitosan or a chitosan comprising composition.

17 Claims, 11 Drawing Sheets

ANTIMICROBIAL AND/OR EPITHELIAL CELL GROWTH STIMULATING SUBSTANCE AND COMPOSITION AND TISSUE DRESSING MATERIAL

CROSS-REFERENCE TO RELATED APPLICATIONS

This application is a continuation of U.S. patent application Ser. No. 13/392,673, filed May 7, 2012, which is a national stage application under 35 U.S.C. § 371 of PCT Application No. PCT/EP2010/062823, filed Sep. 1, 2010, which claims priority to and the benefit of PCT Application No. PCT/EP2009/006323, filed Sep. 1, 2009. U.S. patent application Ser. No. 13/392,673, PCT Application No. PCT/EP2010/062823, and PCT Application No. PCT/EP2009/006323 are incorporated herein by reference in their entirety.

FIELD OF THE INVENTION

The invention relates to a medical use of chitosan and to a pharmaceutical composition comprising the chitosan. The invention further relates to a method of treating a microbial infection and to an aqueous solution comprising chitosan. The invention moreover relates to a chitosan or a pharmaceutical composition comprising a chitosan for an epithelial cell growth stimulating treatment of a patient's tissue and to a method of stimulating the growth of epithelial cells. The invention also relates to a tissue dressing material.

BACKGROUND OF THE INVENTION

The polysaccharide chitosan is the at least partially N-deacetylated derivative of chitin. Chitin can be found widely in the exoskeletons of arthropods, gels, crustaceans and the cuticles of insects. It is usually derived from such natural sources. Chitosan in general is synthetically prepared by hydrolysis of chitin, although it can also be naturally derived directly, e.g. from certain fungi in which it occurs. The different solubilities of chitin and chitosan in dilute acids are commonly used to distinguish between the two polysaccharides. Chitosan, the soluble form, can have a degree of acetylation (DA) between 0% and about 60%, the upper limit depending on parameters such as processing conditions, molecular weight, and solvent characteristics. While soluble in acidic aqueous media, chitosan precipitates at a pH of above 6.3.

Both chitin and chitosan are promising polymers for biomedical applications because of their biocompatibility, biodegradability and structural similarity to the glycosaminoglycans. For comprehensive reviews of potential applications of chitin and chitosan see, e.g., Shigemasa and Minami, "Applications of chitin and chitosan for biomaterials", Biotech. Genetic. Eng. Rev. 1996, 13, 383; Kumar, "A review of chitin and chitosan applications", React. Funct. Polym. 2000, 46(1), 1; and Singh and Ray, "Biomedical applications of chitin, chitosan and their derivatives", J. Macromol. Sci. 2000, C40(1), 69.

Aranaz et al. in "Functional characterization of chitin and chitosan", Curr. Chem. Biol. 2009, 3, 203, discuss the antimicrobial activity of chitosan, including activity against bacteria, yeast, and fungi. A first mechanism discussed involves an interaction with the cell surface of gram-negative bacteria, which interaction is believed to prevent the transport of essential solutes. Another mechanism involves an inhibition of RNA and protein synthesis in the cell nucleus. This theory appears to predict that a relatively low molecular weight and a relatively low degree of acetylation should increase the chitosan's activity. It is, however, also pointed out that some authors have not found a clear relationship between the degree of acetylation and the antimicrobial activity of chitosan. E.g., in a study by Parker et al. 25% acetylated chitosan showed more effective antimicrobial activity compared with that of 10% and 50% acetylated chitosan. Other suggested mechanisms involve the activity of chitosan as a chelating agent, chitosan's activity to interact with flocculate proteins, and a direct disturbance of membrane function in fungi.

The patent application WO 2010/021930 A1 discloses activity of several chitosan derivatives against bacteria including methicillin-resistant *Staphylococcus aureus*.

The patent application US 2009/0117213 A1 discloses a chitosan/alcohol solution that has antiviral, antibacterial and hemostatic effects. In particular, a solution comprising 1.5% chitosan with a molecular weight between 150 and 300 kD (kilodalton) and a degree of acetylation of 5%, the solution further comprising 25% v/v ethyl alcohol showed antibiotic activity in vitro against several strains of bacteria, including moderate activity against methicillin-resistant *Staphylococcus aureus*.

Problem to be Solved by the Invention

It is an object of the invention to provide a new medical use of a chitosan. The invention further aims at providing an improved pharmaceutical composition comprising chitosan for a medical use. Moreover, the invention seeks to provide a new method of treating a microbial infection and an improved pharmaceutical form of chitosan. It is a further objective of the invention to provide a new method of stimulating the growth of epithelial cells. It is another object of the invention to provide an improved tissue dressing material and an improved tissue dressing material.

Solution According to the Invention

According to the invention, the problem is solved by providing a chitosan for use in an antimicrobial treatment of a patient's tissue. The problem is also solved by providing a pharmaceutical composition comprising a chitosan for use in an antimicrobial treatment of a patient's tissue.

The problem is further solved by providing a method of treating a microbial infection, the method comprising the step of administering to a patient an effective amount of a chitosan. The problem is moreover solved by providing an aqueous solution comprising chitosan.

Thereby, the antimicrobial properties of the chitosan are exploited.

According to the invention, the problem is moreover solved by providing a chitosan or a pharmaceutical composition comprising a chitosan for use in an epithelial cell growth stimulating treatment of a patient's tissue. The problem is further solved by providing a method of stimulating the growth of epithelial cells, the method comprising the step of administering to a patient an effective amount of a chitosan or a pharmaceutical composition comprising chitosan. Thereby, the epithelial cell growth stimulation properties of chitosan are exploited. The epithelial cells preferably are human epithelial cells. The epithelial cells preferably are keratinocytes.

Advantageously, the chitosan and the pharmaceutical composition according to the invention can simultaneously provide for an antimicrobial treatment and an epithelial cell growth stimulating treatment. This is particularly advantageous in the treatment of wounds of various types. Some suitable types of wounds are listed further below in the discussion of preferred embodiments of the invention.

The problem is also solved by providing a tissue dressing material that consists of chitosan and by providing a tissue dressing material that is a composition comprising chitosan. It is one achievable advantage of the tissue dressing material according to the invention that due to the antimicrobial properties of the chitosan it can be kept essentially free of a broad range of microbes without the addition of further antimicrobial or antibiotic substances to the tissue dressing material. In particular, the tissue dressing material according to the invention can be kept sterile according to the pertinent hygienic requirements without the addition of further antimicrobial or antibiotic substances to the tissue dressing material.

The tissue dressing material preferably is used for dressing wounds. Advantageously, the tissue dressing material can be used for an antimicrobial and/or an epithelial cell stimulating treatment according to the invention.

A patient in the context of the present invention can be a human or an animal.

PREFERRED EMBODIMENTS OF THE INVENTION

Preferred features of the invention which may be applied alone or in combination are discussed in the dependent claims and in the following description.

In some embodiments of the invention, the chitosan or chitosan containing composition may be applied to the patient in vivo. Alternatively, it may be applied ex vivo to an epithelial cell containing cell culture.

The preferred treatment is for at least one of the following or a combination thereof: preventing the risk of a microbial infection, reducing the microbial load of an existing microbial infection, preventing or reducing the spread of a microbial infection. The chitosan or the pharmaceutical composition according to the invention may act as a barrier to protect of a microbial infection from inside and outside the tissue treated.

The antimicrobial treatment preferably is an antibacterial treatment, exploiting the antibiotic property of the chitosan. Preferred indications include nosocomial infections. Preferred indications include infections with multidrug resistant bacterial strains. The infection preferably is at least one of the following or a combination thereof: methicillin-resistant *Staphylococcus aureus* (MRSA) infection, oxacillin-resistant *Staphylococcus aureus* (ORSA) infection, multidrug-resistant *Clostridium difficile* infection, penicillin-resistant *Streptococcus pneumonia* infection, multidrug-resistent *Pseudomonas aeruginosa* infection, multidrug-resistant *Acinetobacter baumannii* infection, vancomycin-resistant *Enterococcus* infection. Suitable bacteria include gram-positive bacteria, gram-negative bacteria and spore forming bacteria. Suitable bacteria include, for example, *Staphylococcus aureus*, Streptococci (group A), *Streptococcus pyogenes, Borellia burgdorferi, Bacillus anthracis, Erysopelothrix rhusiopathiae, Bartonella henselae, Bartonella quintana, Corynebacterium minutissimum, Staphylococcus epidermides,* Enterobacteriaceae (*E. coli, Klebsiella*), *Haemophilius influenzae, Pasteurella multocida, Franciscella tularensis, Pseudomonas aeruginosa*. However, the antimicrobial treatment may also be an antifungal treatment, e.g. against fungi involved in the athlete's foot disease such as dermatophytes or a treatment against. Suitable fungi and yeast include, for example, *Aspergillus niger, Mucor* (*Mucor pusillus, Mucor plumbeus, Mucor racemosus, Mucor hiemalis*), *Sporothrix, Histoplasma, Coccidioides, Trichophyton, Microsporum, Epidermophyton, Keratomyces, Cryptococcus, Candida albicans, Candida dubliensis, Malassezia furfur*. Similarly, advantageously, the tissue dressing material according to the invention due to the presence of chitosan can be kept essentially free of the above cited microbes without the addition of other antimicrobial or antibiotic substances to the tissue dressing material.

The treatment preferably is a locally confirmed treatment. "Local confined" in the context of the present invention means that the activity of the chitosan or the chitosan containing composition is essentially limited to this tissue to which it is applied and tissue adjacent to the tissue to which it is applied. Preferably, the adjacent tissue, where the chitosan or the chitosan containing composition is also active extends not more than 10 mm (millimeters), more preferably not more than 5 mm away from the tissue to which the chitosan or the chitosan containing composition is applied. Such activity in adjacent tissue can for example be the result of transport (e.g. by diffusion, capillary forces, osmotic transport, cavitation) of active constituents of the chitosan or the chitosan containing composition from the site of application to the adjacent tissue after application. With the locally confined treatment, it can be exploited that the site where the chitosan or chitosan containing composition is applied and thus the activity takes place can be well controlled in order to achieve essentially only a local activity. Advantageously, a systemic activity, i.e. a medical activity in regions of the patient's body where such activity is not required and/or not desirable, can be avoided. The invention can thus reduce side effects and contribute to the swift recovery of the patient.

The preferred locally confined treatment is an external use of the chitosan or the chitosan containing composition. However, an internal treatment is also possible: The chitosan or the chitosan containing composition may for example be injected in a well-defined area of the patient's body, inhaled or swallowed. Preferably, the chitosan or the chitosan containing composition is applied in contact with the tissue to be treated or in contact to tissue surrounding the tissue to be treated.

In a preferred embodiment of the invention, the treatment is a topically confirmed treatment. "Topically confined" in the context of the present invention refers to a "locally confined" treatment, in which the application takes place on a surface of the patient's tissue, for example a part of the patient's skin. With this embodiment of the invention it can advantageously be achieved that the activity of the chitosan or the chitosan containing composition can be limited to such surface (e.g. the skin) and an area immediately beneath the surface, preferably less than 10 mm, more preferably less than 5 mm beneath the surface. Preferred surfaces include healthy biological surfaces, infected surfaces, and wounds. The surfaces may be topically accessible for example by direct application, such as by droplets, rinsing, spraying or aerosol inhalation. Surfaces may include i.a. outer surfaces, surgically generated surfaces, and surfaces of the nasal, laryngeal and pulmonary cavities, including the alveoli.

The treatment according to the invention may be for lasting prevention and/or acute treatment.

Preferably, the chitosan or the chitosan component of the chitosan containing composition exhibits a specific pharmaceutical activity for the microbial infection to be treated if the chitosan or the chitosan component has a concentration higher than 1%, more preferably higher than 0.1%, more preferably higher than 0.01% weight per volume in the site of action, e.g. the tissue to be treated. On the other hand, the chitosan or the chitosan component of the chitosan containing composition preferably exhibits no specific pharmaceutical activity for the microbial infection to be treated if the chitosan or the chitosan component has a concentration lower than 0.001% weight per volume, more preferably lower than 0.01%, more preferably lower than 0.1%. Thereby, it can be achieved that the pharmaceutical activity is locally confined to a site of action such as a tissue to be treated in which a sufficiently high concentration of the chitosan or chitosan component is maintained.

Preferably, the chitosan or the chitosan component of the chitosan containing pharmaceutical composition exhibits a specific pharmaceutical activity for the microbial infection to be treated if the chitosan or the chitosan component has a concentration higher than 100 µM/L (micromol per liter), more preferably higher than 10 µM/L, more preferably higher than 1 µM/L in the site of action, e.g. the tissue to be treated. On the other hand, the chitosan or the chitosan component of the chitosan containing pharmaceutical composition preferably exhibits no specific pharmaceutical activity for the microbial infection to be treated if the chitosan or the chitosan component has a concentration lower than 0.1 µM/L, more preferably lower than 1 µM/L, more preferably lower than 10 µM/L.

The chitosan or the chitosan containing composition according to the invention preferably is applied to the surface of the tissue to be treated. The tissue to be treated preferably in one dimension (typically the depth dimension) is less than 10 mm, more preferably less than 5 mm thick. In this embodiment it is exploited that the chitosan or chitosan containing composition according to the invention can be applied to a surface of such tissue and a sufficient concentration of the chitosan or chitosan component in the tissue can be achieved, preferably by diffusion, to exhibit a activity.

Tissues preferably treated include chronic wounds, post-surgery wounds, cuts, abrasions, burns, razor burn, bedsore, ulcerous tissue, wounds caused by viruses which tend to become ulcerous, tissue affected by dermatoses, for example athlete's food disease, diabetic foot and psoriasis, insect bites, tissues affected by acne, in particular acne vulgaris, tissue affected by lupus erythematosus, in particular malar rash, mucosal tissue, tumor tissue, tonsils, tissue in the genital area and tissue in body cavities or orifices. The invention can also be of use when surgery is performed on a patient. When treating wound tissue, the chitosan or chitosan containing composition may be applied into or onto the wound.

The preferred chitosan is a native chitosan. The term "native chitosan", in the context of the present invention refers to the defined chemical entity chitosan, which is a poly(N-acetyl-D-glucosamine-co-D-glucosamine) copolymer or a poly(D-glucosamine) homopolymer. Any cross-linked or otherwise chemically modified chitosan is considered a chitosan derivative, having different properties than native chitosan. In the context of the present invention the term "native chitosan" includes both the chitosan base and chitosan in the form of a chitosan salt, dissolved or undissolved. When in the context of the present invention it is referred to "chitosan" in general, this can be any form, salt or base, of native chitosan or any derivative of a poly(N-acetyl-D-glucosamine-co-D-glucosamine) copolymer or a poly(D-glucosamine) homopolymer, cross-linked and/or otherwise modified.

Preferably, the chitosan's degree of acetylation (DA) is 40% or less, preferably 20% or less, preferably 10% or less. Preferably, the chitosan is deacetylated. In the context of the present invention the term "deacetylated chitosan" means that the chitosan's DA is less than 2.5%. Such low DA can contribute to the chitosan's antimicrobial activity. In a preferred chitosan or chitosan containing composition according to the invention, the deacetylated chitosan's or the deacetylated native chitosan's DA is 2% or less, preferably 1.5% or less, more preferably 1% or less, more preferably 0.5% or less. Advantageously, such extremely low degrees of acetylation can further improve the antimicrobial properties of the invention. Also, lysozymal biodegradation of the chitosan or its dissolution can be limited or prevented.

The DA can be obtained by means of $^1$H NMR spectroscopy as, e.g., disclosed in Lavertu et al., "A validated $^1$H NMR method for the determination of the degree of deacetylation of chitosan", J. Pharm. Biomed. Anal. 2003, 32, 1149. "Deacetylated native chitosan" in the context of the present invention refers to chitosan that is both native and deacetylated according to the above definitions.

The preferred chitosan can be prepared by a method that involves at least two deacetylation steps. Two deacetylation steps are separated (and thus distinguished from a single deacetylation step) at least by a washing step in which by-products of the deacetylation, such as acetate, are at least partly removed. Preferably, at least one, more preferably all deacetylation steps are hydrolysis steps. A hydrolysis step may involve mixing the chitosan with a solution of a hydroxide such as sodium hydroxide. Preferably, during a hydrolysis step, the chitosan is exposed to a temperature higher than room temperature, e.g. 100° C. Preferably, at the end of each deacetylation step, the chitosan is washed, e.g. in water. Moreover, at least at the end of the last deacetylation step, preferably at the end of each deacetylation step, the chitosan is dried.

In certain embodiments of the invention, between two deacetylation steps an acetylation step is performed. A preferred acetylation step may involve mixing the chitosan or acidic chitosan solution with an organic solvent, followed by treatment with a carboxylic anhydride at room temperature. Preferably, at the end of the acetylation step, the acetylated chitosan is washed and dried.

Preferably, the chitosan is present in two fractions with regard to their solubility at a certain pH in the sense that at this pH one chitosan fraction is insoluble while the other is soluble. Thereby, it can advantageously be achieved that at this pH the insoluble fraction can take a solid or gel-like form, preferably that of a hydrogel, and can thus act as a reservoir or matrix holding the soluble fraction, which soluble fraction can diffuse from the reservoir or matrix into the target tissue or into the patient's blood.

Preferably, a fraction of more than 10% of the chitosan being present in a form that is insoluble at least at a pH of 6.5, more preferably at least at any pH between 6.5 and 8.5. More preferably, the fraction comprises more than 20%, more preferably more than 50% of the chitosan. More preferably, the fraction is also insoluble at a pH of 6.3, more preferably at least at any pH between 6.3 and 8.5. In this embodiment of the invention, advantageously, the chitosan or the chitosan containing composition can take the form of a solid or a gel, preferably a hydrogel.

Preferably, a fraction of more than 0.1% of the chitosan is present in a form that is soluble at a pH of 6.5. More preferably, the fraction comprises more than 1%, more preferably more than 5%, more preferably more than 10% of the chitosan. More preferably, the fraction is also soluble at a pH of 7.0, more preferably also at a pH of 7.5. With this embodiment of the invention, it is advantageously achievable that said fraction of the chitosan can readily diffuse into the tissue to be treated.

The terms "soluble" and "dissolve" in context with chitosan is meant to refer to a process of mass loss of chitosan without molecular weight decrease (i.e., without decrease in polymer chain length) due to solubility in an aqueous environment. This is to be distinguished from "degradation", which is the process of molecular weight decrease due to depolymerisation of chitosan.

Typically, the pH at which a certain chitosan is soluble depends on its chain length and therefore on its molecular weight. Moreover, typically, the chitosan or the chitosan component of the composition according to the invention contains a distribution of molecular weights. Preferably, a fraction of more than 10% of the chitosan has a molecular weight of 10 kD (kilodalton) or more. More preferably, the fraction comprises more than 20%, more preferably more than 50% of the chitosan.

Preferably, a fraction of more than 0.1% of the chitosan has a molecular weight of less than 10 kD. More preferably, the fraction comprises more than 1%, more preferably more than 5%, more preferably more than 10% of the chitosan. More preferably, the average molecular weight of this fraction is greater than 1 kD.

Preferably, the chitosan is part of a composition comprising other components in addition to the chitosan. However, chitosan preferably is the main component of the composition. In the context of the present invention, the expression "main component" with regard to chitosan or a type of chitosan (such as chitosan in general, deacetylated chitosan, native chitosan or deacetylated native chitosan) means that the respective type of chitosan makes up at least 50% by weight of the composition. Thus, if e.g. the chitosan or chitosan containing composition material is provided as a solid or gel-like film to be applied to the tissue, this film is required to be made up of the respective type of chitosan by at least 50% by weight. In the case of the liquid chitosan containing composition, the expression "main component" with regard to the constituent(s) other than water in the aqueous mixture means that at least 50% by weight of the combination of all constituents other than water must be the respective type of chitosan.

The preferred composition is free of alcohol. This has the advantage of the composition being less irritating to the tissue to which it is applied. More preferably, the composition is free of alcohol or any other organic solubilizer or stabilizer. More preferably, the chitosan containing composition is free of organic solvents in general, including, in addition to alcohols, esters, alkanes, halogenated solvents, amines and amides. It may, however, frequently contain an organic acid; organic acids are not considered organic solvents in the context of the present invention. Preferably, the composition material comprises no additional preservative. It preferably is free of aseptic agents, antioxidants and surfactants, thereby reducing the risk of toxic or allergic reactions.

In some embodiments, the chitosan containing composition comprises at least one pharmaceutically active and/or bioactive constituent other than chitosan. Suitable bioactive constituents may e.g. be proteins, peptides or derivatives thereof, nucleic acids or derivatives thereof, low molecular weight compounds active as drugs, such as antibiotics or anti-inflammatory drugs, or agonists or antagonists of the innate immune system, or stimulating or differentiating growth factors for stimulating or differentiating growth of at least one sub-type of cells, or resins with affinity to certain components to be extracted from a wound surface, or dissolved or dispersed compounds or polymers with decorative functions such as light absorbing, fluorescent or phosphorescent or light reflecting particles. Alternatively, or in addition, the chitosan containing composition may comprise biological cells.

In one preferred embodiment of the invention, the chitosan containing composition comprises a pH-sensitive dye for visually indicating the pH at the site of application. The pH can be used as a proxy for indicating the condition of the tissue at the site of application. In a preferred embodiment of the invention, the composition is transparent, in particular if it is in the solid, gel-like or solidified form as explained in more detail below. Advantageously, in external applications of the composition this can make it easier for a physician to inspect the tissue treated, in particular if it is a wound tissue. In some embodiments, the chitosan or the chitosan containing composition is a transparent solid film. In others the composition is a mixture such as a dispersion, a suspension or a solution that forms a transparent film when applied to the tissue. Also, in the case that the composition comprises a pH-sensitive dye the colour of the dye can be judged due to the transparency of the chitosan containing composition.

A preferred composition is a liquid. In general, after application, at least a fraction of the liquid composition will solidify, i.e. the composition will turn into a solid or a gel, for example a hydrogel. In some embodiments of the invention, removal, preferably evaporation, of the solvent that was present in the liquid composition when it was applied causes or at least contributes to the solidification. Additionally or alternatively, solidification may be caused or contributed to by other factors such as chemical or physical cross-linking of polymeric components of the composition.

It is achievable advantage of the invention that after application of the composition the concentration of the chitosan may increase due to removal, preferably by evaporation, of other components, in particular of a solvent. Such removal preferably occurs spontaneously, that is without requiring any further measures to be taken to initiate the concentration process such as applying additional chemicals or heat. In other words: The material is self-concentrating. Preferably, to promote the self-concentration process, a chitosan material or the chitosan containing composition is chosen that is non-hygroscopic when applied.

Preferably, the chitosan containing composition is an aqueous mixture, e.g. a dispersion or a suspension, more preferably a solution, i.e. it comprises water as the mixture medium or solvent, respectively. Moreover, in some embodiments of the invention it may comprise a co-solvent, for example an alcohol such as isopropanol. This can have the advantage of faster evaporation of the solvent if a fast solidification of (a fraction) of the composition is required. Other embodiments, as discussed before, are free of alcohol, preferably free of organic solvents in general, in order to avoid tissue irritation.

The solute or more generally the constituent(s) of the composition that remain(s) once the mixture medium is removed upon solidification of the composition preferably comprises, more preferably consists of a chitosan salt such as the salt of native chitosan or the salt of a chitosan derivative. Preferred salts are those derived from the dissolution of a chitosan such as native chitosan, in an inorganic acid, such as hydrochloric acid, or an organic acid selected from the group of monobasic or multibasic organic acids having 2 to 12 carbon atoms and a first pKa value between 1 and 5, such as acetic acid, citric acid, lactic acid, malic acid, succinic acid, mandelic acid, oxalic acid, tartaric acid, ascorbic acid, etc.

Preferably, chitosan, more preferably native chitosan, is the main component other than water of the liquid composition. Preferably at least 70% by weight of the constituent(s) of the mixture other than water is chitosan, preferably native chitosan. A particularly preferred mixture essentially only consists of chitosan, preferably native chitosan, and water. The preferred mixture is acidic.

The concentration of the chitosan in the liquid composition preferably is less than 15%, more preferably less than 10%, more preferably less than 7.5%, more preferably less than 5% more preferably less than 2.5%, more preferably less than 1% by weight. The concentration of the chitosan in the liquid composition preferably is more than 0.1%, more preferably more than 0.25%, more preferably more than 0.5%, more preferably more than 1% by weight.

For application, the liquid chitosan containing composition preferably is sprayed onto the tissue and the mixture medium or solvent subsequently is allowed to evaporate to form a solid or gel-like film. Typically the film is between 0.1 and 50 μm thick, preferably between 1 and 25 μm. It has a surface area sufficient to cover the tissue to be treated such as a wound, and, preferably, also some of the surrounding tissue. Accordingly, the chitosan containing composition preferably is provided in or in combination with a spraying apparatus for spraying the chitosan containing composition onto the tissue of the patient. The preferred spraying apparatus comprises a container for storing the chitosan containing composition. It may also comprise pressurized gas for expelling the chitosan containing composition. The composition can be provided in two or more liquid components that are mixed shortly before or during application of the chitosan containing composition to the tissue. In this case, the spraying apparatus may comprise several containers and/or several spraying apparatus may be provided, each containing one of the liquid components. Alternatively, the liquid chitosan containing composition may be brushed onto the tissue or applied by means of a sponge, a spatula, a pipette, or gauze. Accordingly, the composition preferably is provided in combination with a sponge, a brush, a spatula, a pipette or gauze for applying the chitosan containing composition or at least a constituent of the chitosan containing composition to a tissue.

Alternatively, the chitosan or the composition according to the invention is provided in a solid or gel-like form, for example as a hydrogel. Preferably, the chitosan or the composition has the form of a film. A film is particularly advantageous for the treatment of an extended area of a tissue, e.g. the skin. Preferably, the film has a surface area sufficient to cover the tissue to be treated, such as a wound, and preferably also some of the surrounding tissue. The preferred film has a smooth surface, preferably with an average roughness $R_a$ of 1 μm (micrometer) or less, more preferably 0.3 μm or less, more preferably 0.1 μm or less. Advantageously, a smooth surface can reduce the formation of mechanical anchoring to the tissue to which it is applied, thereby facilitating removal of the chitosan or the composition after use. The preferred film is less than 10 mm thick, more preferably less than 1 mm. Typically, the film when dry is between 0.5 and 500 μm thick, preferably between 5 and 100 μm, more preferably between 10 and 50 μm, more preferably between 20 and 30 μm. Alternatively, the solid or gel-like chitosan or chitosan containing composition may have the shape of a fiber or a tube. A typical fiber or tube is between 10 μm and 10 mm (millimeters) in thickness and between 1 mm and 100 cm (centimeters) in length.

Preferably, at least 70%, more preferably at least 90%, more preferably at least 95% by weight of the solid or gel-like composition is chitosan, preferably native chitosan.

The preferred solid or gel-like chitosan or composition comprising chitosan is at least partly water-soluble. In other words, at the time it is provided for being applied to the patent's tissue it can be dissolved at least partly in water at neutral pH. The chitosan may for example be a chitosan salt, e.g. the salt of native chitosan or a chitosan derivative. It is an achievable advantage of this embodiment of the invention that the chitosan or chitosan containing composition adheres well to the tissue. Thereby, it can be avoided that chitosan or the chitosan containing composition prematurely detaches from the tissue. This embodiment of the invention advantageously exploits the fact that chitosan salt is soluble in an aqueous solvent of neutral pH. Thus, wet or pre-wetted tissue can liquefy the surface of the chitosan or chitosan containing composition, providing for a durable contact with the tissue. Preferred salts are those derived from the dissolution of a chitosan such as native chitosan, in an inorganic acid, such as hydrochloric acid, or an organic acid selected from the group of monobasic or multibasic organic acids having 2 to 12 carbon atoms and a first pKa value between 1 and 5, such as acetic acid, citric acid, lactic acid, malic acid, succinic acid, mandelic acid, oxalic acid, tartaric acid, ascorbic acid, etc. In an alternative embodiment of the invention the chitosan is present in the form of the chitosan base.

Preferably, a chitosan salt, more preferably a salt of native chitosan, makes up the main component of the solid or gel-like chitosan containing composition. More preferably, at least 70%, more preferably at least 90%, more preferably at least 95% by weight of the solid or gel-like chitosan containing composition is a chitosan salt, preferably a salt of native chitosan.

After the liquid chitosan containing chitosan containing composition or the solid or gel-like water soluble chitosan or chitosan containing composition is applied, and in the case of a liquid composition during or after solidification, it preferably is allowed to transform into a water-insoluble form, e.g. a chitosan base. This transformation may, for example, occur due to evaporation of a constituent of the chitosan containing composition upon contact with air. It may also be a result of an interaction of the chitosan with a body fluid and/or the tissue itself; for example the relatively high pH of blood and/or the attachment of proteins present in the blood to the chitosan may induce the transformation. Alternatively or additionally, transformation may be achieved by applying a transformation medium, e.g. an aqueous alkaline solution, to the chitosan or chitosan containing composition. Advantageously, it can be achieved that after transformation the chitosan or chitosan containing composition remains in place and therefore pharmaceutically active under normal condition, e.g. when the tissue is cleaned under tap water (neutral pH) or when soap (alkaline) is applied. The chitosan or composition comprising chitosan can be provided in combination with the transformation medium as a kit.

In a preferred embodiment of the invention, the chitosan or the chitosan containing composition has a pH below 8.5, preferably below 8, particularly preferably around 7 to 7.5. The preferred pH is above 6.3, more preferably above 6.5. It is an achievable advantage of this embodiment of the invention that one fraction of the chitosan can be soluble and the other insoluble, acting as a reservoir or matrix for the soluble fraction. Also advantageously, the pH is close to that of healthy tissue, thereby avoiding irritation or damage of the tissue to which the chitosan containing composition is applied.

In another preferred embodiment of the invention, the chitosan or the chitosan containing composition has a pH of below 6.3, preferably below 6, particularly preferably around 5 to 5.5. The preferred pH is above 3.0, more preferably above 4.0, more preferably above 4.5. This embodiment is particularly advantageous for liquid chitosan compositions, as at a pH of 6.3 chitosan in general is soluble in an aqueous medium. This embodiment of the invention moreover preferably applies to external applications of the chitosan or chitosan containing composition. It is an achievable advantage of this embodiment of the invention that the pH is close to that of the surface of healthy skin, thereby avoiding irritation or damage of the tissue to which the chitosan or chitosan composition is attached. Moreover, due to subsequent transformation, the pH may rise above 6.3, more preferably above 6.5, so that that one fraction of the chitosan can remain soluble while the other turns insoluble, acting as a reservoir or matrix for the soluble fraction.

The inventors have found that the presence of glycerol in the solid chitosan or chitosan containing composition can accelerate the transformation from a water-soluble state into a state in which the product is only soluble in an acid liquid solvent. For example, in the case of a native chitosan salt as a chitosan salt, transformation can be accelerated from approximately one month to a mere week. Without limiting the invention to a specific theory, the inventors believe that the acceleration may be due to the glycerol's effect of disrupting the crystalline structure of the chitosan salt. Advantageously, the faster transformation allows the beneficial effects of the transformation to set in earlier. The glycerol content preferably makes up at least 10%, more preferably at least 15%, more preferably at least 20% by weight of the solid composition's chitosan salt content by weight. The glycerol preferably is present at a concentration of more than 10%, more preferably more than 15%, more preferably more than 20% by weight. The glycerol preferably is present at a concentration of less than 60%, more preferably less than 45%, more preferably less than 30% by weight.

The chitosan or the composition comprising chitosan according to the invention preferably is provided as a kit in combination with a detachment solvent to facilitate detachment of the water-insoluble solid or gel-like chitosan or the chitosan containing composition from the patient's tissue after use, e.g. to be replaced or at the end of a therapy. In the context of the present invention, a "detachment solvent" is a liquid that can be applied to the chitosan or the chitosan containing composition when it is in a solid or gel-like state and that can facilitate detachment of the product from the tissue, preferably by at least partly dissolving and/or swelling it. The preferred detachment solvent can reduce the adherence of the product to the patient's tissue. Thus, with the detachment solvent it can be avoided that the tissue is damaged during removal of the chitosan or the chitosan containing composition, and in particular it can be avoided that when the chitosan or chitosan containing composition is removed, parts of the tissue beneath it that adhere to the chitosan or the pharmaceutical composition are torn away. Amongst other cases, this can be of great advantage where the chitosan or the chitosan containing composition is applied to a wound as a wound dressing or as part of a wound dressing, because wound tissue can be very sensitive to mechanical stress. With the invention, therefore, irritation or damage of the regenerating tissue can be avoided. By providing the chitosan or the chitosan containing composition together with the detachment solvent in a kit it can considerably improve compliance in the sense that the patient is less likely to attempt to separate the chitosan or chitosan containing composition from the tissue without previous application of the detachment solvent. The kit according to the invention can also prevent the user from applying another, unsuitable or possibly even harmful solvent.

Preferably, the detachment solvent is an aqueous solvent, e.g. distilled water, an aqueous solution of ionic compounds, such as an aqueous sodium chloride solution, a buffered solution, such as an acetic acid/acetate buffered solution, or an aqueous solution of non-ionic compounds, such as an aqueous glucose solution. Advantageously, water as a solvent is less irritating to the skin than many organic solvents. While in principle, the aqueous detachment solvent according to the invention may in addition to water comprise one or more co-solvents other than water, e.g. an organic co-solvent such as isopropanol or another alcohol, the preferred detachment solvent is free of organic solvents, including alcohols, esters, alkanes, halogenated solvents, amines and amides. It may, however, frequently contain an organic acid; organic acids are not considered organic solvents in the context of the present invention.

The detachment solvent preferably is acidic. This embodiment of the invention exploits the fact that the solubility of chitosan can be pH-dependent. Thus, advantageously, the pH of the detachment solvent can be selected from a range in which all chitosan fractions dissolve. The preferred pH of the detachment solvent is below 6.5, more preferably below 6.3. More preferably, the pH of the detachment solvent is below 6, more preferably below 5.5, more preferably below 5. The pH of the detachment solvent preferably is above 3.5. Thereby, advantageously irritation of the tissue due to high acidity of the detachment solvent can be avoided. More preferably, the pH of the detachment solvent is above 4, more preferably above 4.5. A preferred detachment solvent comprises a surfactant, e.g. a polysorbate such as Tween. Alternatively or in addition it may comprise substituted or unsubstituted polyalkyleneoxide, such as polyethylene glycol or polypropylene glycol esters. It has been found that the presence of such additives can considerably facilitate detachment of the solid, gel-like or solidified liquid chitosan or chitosan containing composition.

The amount of detachment solvent provided in the kit is at least 5 times per weight, more preferably at least 50 times per weight of the amount of the chitosan provided in the kit. By providing a sufficient amount of detachment solvent, it can be avoided that the pH of the chitosan or the chitosan containing composition falls under a certain threshold. For application, the detachment solvent may be sprayed or brushed or applied by means of a sponge, a spatula, a pipette or gauze. Accordingly, a preferred kit contains a sponge, a brush, a spatula, a pipette or gauze for applying the detachment solvent. The detachment solvent may for example be provided in a sealed bottle or a disposable pipette, or by means of gauze, a sponge or a gel soaked with the detachment solvent. It may also be provided in a spraying apparatus. The preferred spraying apparatus comprises a container for storing the detachment solvent. It may also comprise pressurized gas for expelling the detachment solvent.

A preferred kit according to the invention comprises both a solid or gel-like chitosan or composition comprising chitosan and a liquid composition comprising chitosan. In a preferred method according to the invention, first the liquid and subsequently the solid or gel-like chitosan of chitosan containing composition is applied. Preferably in this method, the solid or gel-like product is applied before the product has solidified. The inventors have found that the liquid product can facilitate attachment of the solid or gel-like product to the target tissue. This is particularly true for water-soluble solid or gel-like chitosans or compositions comprising chitosan and as compared to an alternative method in which the water-soluble solid or gel-like chitosan or chitosan containing composition is wetted with water before attachment. This is because the latter method has been found to frequently lead to an undesirable deformation of the solid or gel-like chitosan or chitosan containing composition, which deformation can be avoided by the application of the liquid chitosan containing composition for attachment of the solid or gel-like chitosan or chitosan containing composition. Preferably, in the kit, the liquid composition is one of the preferred liquid chitosan containing compositions described herein. Similarly, the solid or gel-like chitosan or composition comprising chitosan is one of the preferred solid or gel-like chitosans or chitosan containing compositions described herein. Preferably, the liquid compositions and/or the solid or gel-like chitosan or chitosan containing composition and the detachment solvent are provided in separate containers.

The chitosan or pharmaceutical composition comprising chitosan according to the invention may be applied as a tissue dressing, preferably a wound dressing, or it may form part of a tissue dressing or wound dressing. Similarly, the tissue dressing material according to the invention preferably is part of a tissue dressing comprising other components. In a preferred embodiment of the invention, the chitosan or the chitosan containing composition is part of a tissue dressing that comprises a first layer, which layer is formed of the chitosan or composition, and at least another layer formed of another material, this other layer acting as a support. In particular, the support advantageously can help preventing premature detachment of the tissue dressing from the tissue. The support preferably is located at the side of the tissue dressing opposite to the side that is in contact with the tissue. Preferably, the support is adjacent to the chitosan or chitosan containing composition. The support according to the invention is particularly advantageous if the respective type of chitosan, preferably deacetylated native chitosan, is provided in the tissue dressing material in the form of the chitosan base, as the chitosan base in general adheres less well to tissue than a chitosan salt containing tissue dressing material. The support may for example be a woven fabric, foam or a perforated film. The support may for example be of natural materials such as cotton or a natural or synthetic polymer. Suitable polymers include biodegradable polymers, such as polyesters, polyorthoesters, polycarbonates, polyanhydrides, polyurethanes, polyphosphazenes, polyphosphoesters, polysaccharides, polypeptides, as well as derivatives, copolymers, and blends based on these polymers. Suitable polymers also include biodissolvable polymers, such as polyvinyl alcohol, polyvinyl acetate, poly-N-vinyl pyrrolidone, polyethylene glycol, polypropylene glycol, polysaccharides, polypeptides, as well as derivatives, copolymers, and blends based on these polymers. Furthermore, the support may consist of a non-biodegradable/non-biodissolvable polymer, such as silicones, polyurethanes, polyethylene terephthalate, polytetrafluoroethylene, polysulfones, polyethersulfones, polyether ether ketones, polycarbonates, polymethacrylates, polysaccharides, polypeptides, as well as derivatives, copolymers, and blends based on these polymers.

A preferred tissue dressing according to the invention comprises a first layer, which layer is formed of the chitosan or chitosan containing composition, and another layer formed of another material, this other layer acting as an at least partial moisture barrier. In other words the other layer can prevent or at least delay the evaporation of water during treatment of the tissue with the tissue dressing according to the invention. This can be of particular advantage when the tissue dressing is applied to dry wounds. The other layer preferably is located at the side of the layer of the tissue dressing opposite to the side that is in contact with the tissue. Preferably, the other layer is adjacent to the chitosan or chitosan containing composition. The invention also encompasses tissue dressings that have both a support layer and another layer that acts as an at least partial moisture barrier. Of course both functions, that of a support and that of an at least partial moisture barrier, can also be fulfilled by a single other layer. The other layer may for example be of silicone or another polymer or polymer composition from the groups of polymers listed above. Typically the other layer is between 10 and 1000 µm thick, preferably between 50 and 500 µm. In some embodiments of the invention, the other layer is perforated. The holes of the perforation typically are between 10 and 1500 µm in diameter, preferably between 50 and 1000 µm. In an alternative embodiment of the invention, instead of the moisture barrier a layer is provided that can take up fluid, e.g. wound exudate. A suitable material may for example be polysaccharide-based hydrogels or hydrocolloids including cellulose derivatives, or polyurethane foams. This can be of particular advantage when the tissue dressing is applied to wet wounds.

In a preferred embodiment of the invention, the chitosan or chitosan containing composition, preferably the tissue dressing, is provided in a container that can prevent transformation of the chitosan or chitosan containing composition from its liquid or water-soluble state to its water-insoluble state as long as it is in the container and the shelve life has not yet expired. Preferably, the container is vapour proof, more preferably it is essentially airtight. Moreover, in some embodiments of the invention, the chitosan or chitosan containing composition on its side which is intended to be applied in contact with the patient's tissue is covered with a strippable cover sheet. The cover sheet is vapour proof, more preferably air-impermeable.

This can contribute to preventing premature transformation of the chitosan or chitosan containing composition from its liquid of water-soluble state to its water-insoluble state before it is applied to the patient's tissue.

The preferred chitosan or chitosan containing composition has a water uptake capacity of less than 1500% by weight, more preferably less than 100%, more preferably less than 80%. Thereby it is advantageously achievable that a degree of humidity that is favourable for wound healing can be maintained under the tissue dressing as applied to a wound site. Preferably, the chitosan or chitosan containing composition in a solid or gel-like form has a water-uptake capacity of more than 25%, more preferably more than 50%. Advantageously this embodiment of the invention is suitable for absorbing exudative fluids and toxants. In a particularly preferred embodiment of the invention, the water-uptake capacity of the chitosan or chitosan containing composition is between 65 and 75%.

BRIEF DESCRIPTION OF THE DRAWINGS

The invention is illustrated in greater detail with the aid of the following figures.

DETAILED DESCRIPTION OF EMBODIMENTS OF THE INVENTION 1. 1H NMR Spectroscopy

Figure 1:
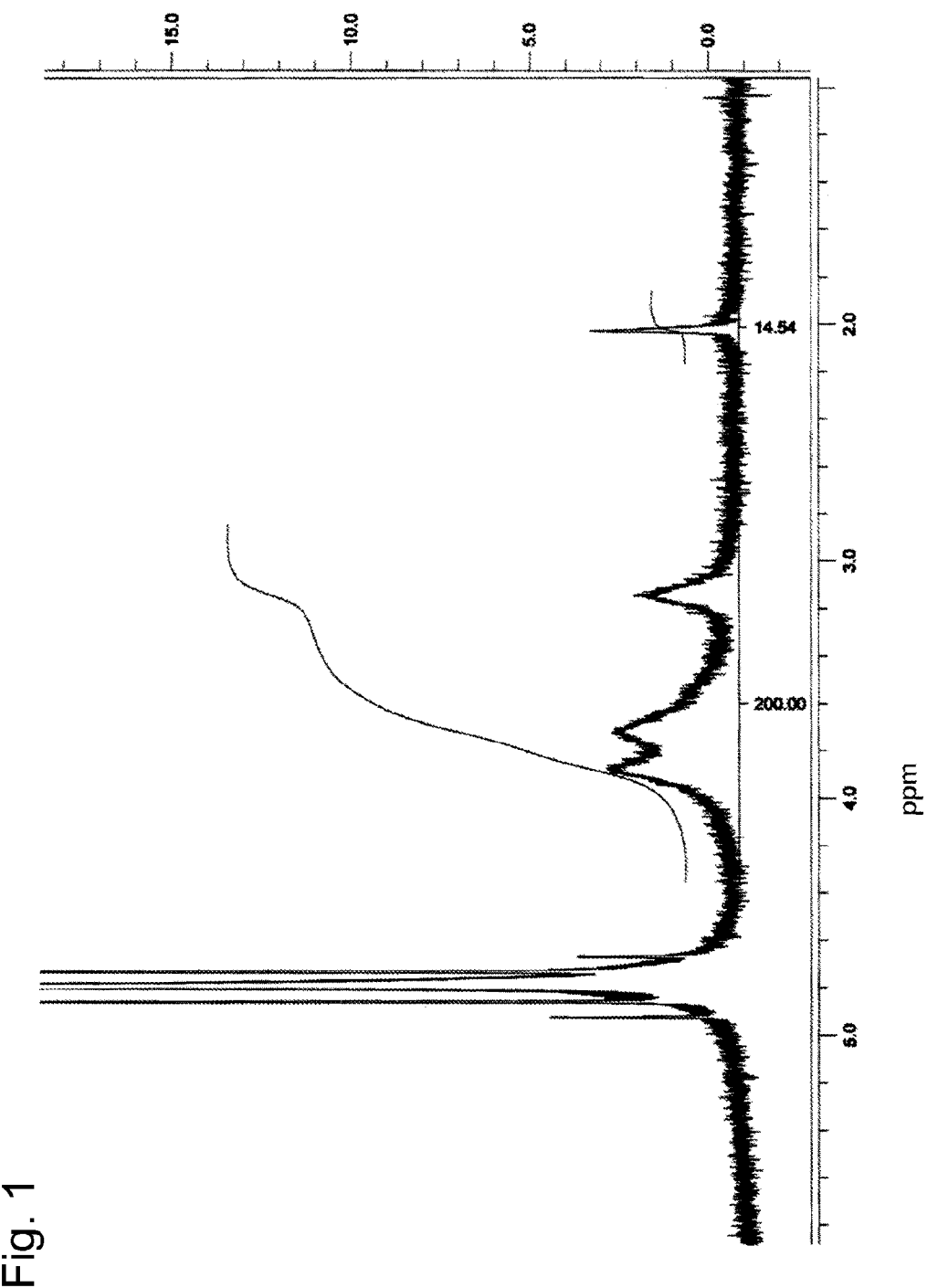
FIG. 1 shows an $^1$H NMR spectrum of native chitosan as purchased.
Figure 2:
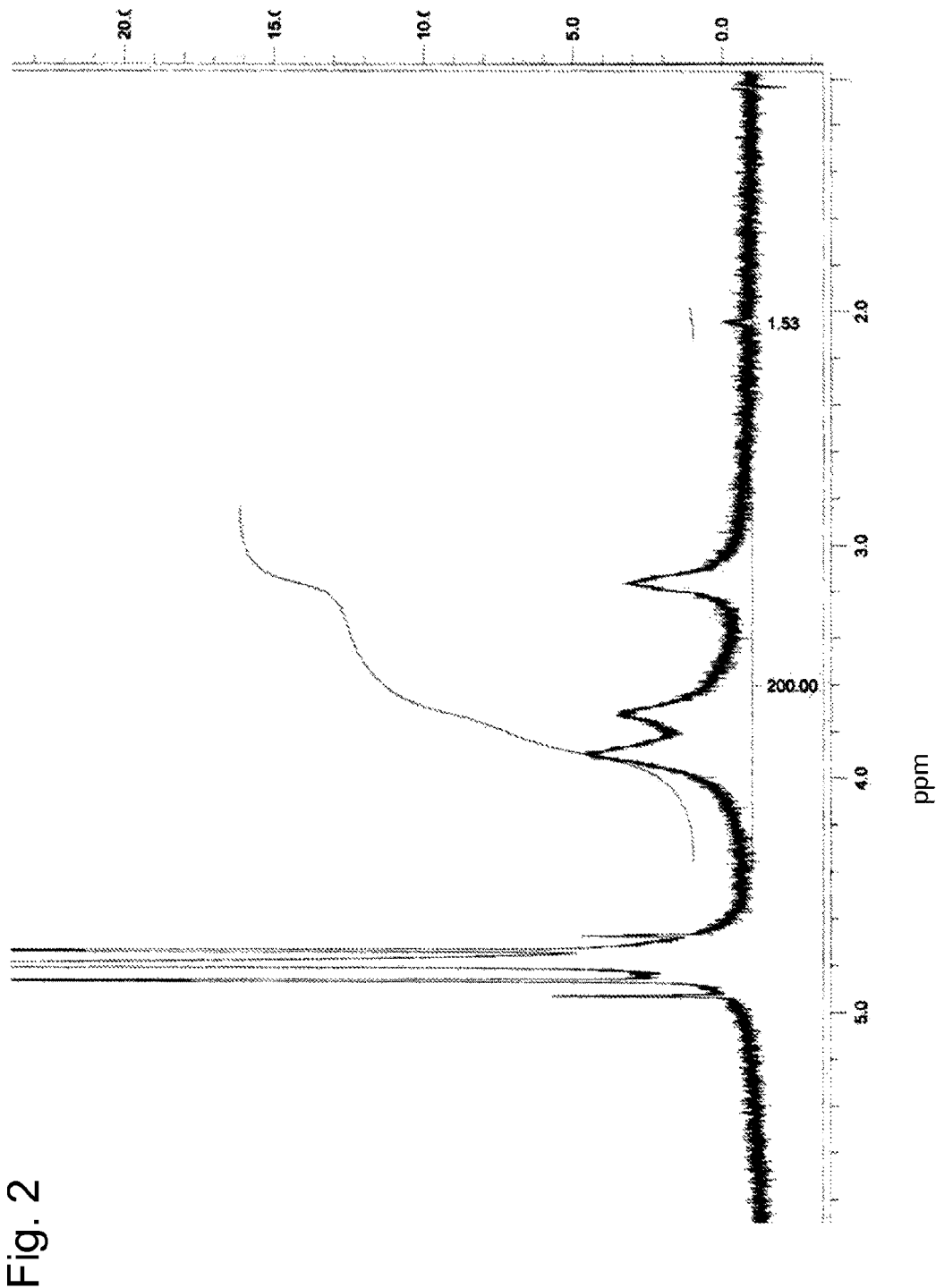
FIG. 2 shows an ¹H NMR spectrum of native chitosan essentially deacetylated after further hydrolysis steps.

The chitosan used in the examples below was obtained in the form of fine flakes from Cognis (Germany). The degree of acetylation (DA) was determined by 1H NMR spectroscopy. FIG. 1 shows an 1H NMR spectrum obtained from this commercially available chitosan. FIG. 2 shows a corresponding 1H NMR spectrum obtained from chitosan deacetylated after further hydrolysis steps applied to the commercial product as described further below. In both cases, chitosan was analyzed in a mixture of 0.25% DCl in D20 at a chitosan concentration of approximately 0.5% (w/v). The spectra were recorded using a Bruker AC200 spectrometer. NMR chemical shifts ($\delta$, in ppm) were referenced to the signal of HDO ($\delta$=4.8 ppm). The DA, calculated by comparing the integrated area under the peaks associated with H2-H6 of the D-glucosamine subunit with that of the methyl group, was determined as 14.5% for the native chitosan as purchased, and 1.5% for the deacetylated native chitosan.

2. Synthesis of Low-DA Chitosan

For further hydrolysis, 50 g (grams) of the chitosan flakes as obtained from the supplier Cognis were placed in a glass container, and 500 g of a 45% aqueous sodium hydroxide solution were added. The glass container was well shaken to mix the components, and placed in an oven for 2 hours at 100° C. It was then removed from the oven, and 500 mL (milliliters) of distilled water were added. The mixture was filtered through a glass frit. Then, the chitosan was washed with distilled water until the pH of the filtrate reached 6.5, and dried at 100° C. for 4 h (hours). This hydrolysis treatment was then repeated, resulting in 42 g of deacetylated native chitosan having a degree of acetylation of 1.5% as determined by 1H NMR spectroscopy.

3. Preparation of Chitosan Solutions (Solutions A1, A2 and A3)

15 g of the thus obtained native chitosan having a DA of 1.5% were dissolved in 500 mL of a 2% aqueous acetic acid by gently shaking for 24 h. Below, the material is referred to as chitosan solution A1.

A second chitosan solution with a chitosan concentration of 1.5% was obtained by addition of 500 ml of distilled water to 500 ml of solution A1. Below, the material is referred to as chitosan solution A2.

A third chitosan solution with a chitosan concentration of 0.75% was obtained by addition of 1500 ml of distilled water to 500 ml of solution A1. Below, the material is referred to as chitosan solution A3.

4. Preparation of a First Example of a Solid Film-Type Chitosan (Chitosan B)

Two portions of 144 mL each of solution A2 were poured into two square-shaped moulds, 24×24 cm² (square centimetres) in size, and left in a dust-free environment for drying at room temperature. The resulting film was removed from the first mould, and sterilized using a 10 kGy (kilogray) electron beam. An approximately 80 μm thick transparent film essentially consisting entirely of deacetylated native chitosan acetate salt was obtained. Below, the material is referred to as chitosan B.

5. Preparation of a Second Example of a Solid Film-Type Chitosan (Chitosan C)

The dried film from the second mould was placed for 2 hours in a bath containing a solution of 1.5% ammonia in methanol/water 90/10 (v/v). The film was then removed from the bath and dried by storage at room temperature. The film was sterilized using a 10 kGy electron beam. An approximately 80 μm thick transparent film essentially consisting entirely of deacetylated native chitosan base was obtained. Below, the material is referred to as chitosan C.

6. Preparation of a Third Example of a Solid Film-Type Chitosan (Chitosan D1)

144 mL of solution A2 was filtered first through a glass fiber filter (pore size approximately 1 μm), and then through a 0.22 μm filter for sterilization, poured into a square-shaped mould, 24×24 cm² in size, and left in a dust-free environment for drying at room temperature. After 3 days of storage, the resulting film was removed from the mould, transferred in a plastic bag that was then tightly sealed, and sterilized using a 25 kGy (kilogray) electron beam. An approximately 80 μm thick transparent film essentially consisting entirely of deacetylated chitosan acetate salt was obtained. Below, the material is referred to as chitosan D1.

7. Preparation of a Fourth Example of a Solid Film-Type Chitosan (Chitosan D2)

In a slightly modified procedure, 4% (w/w) glycerol was added to the filtered solution of the previous example before pouring it into the square-shaped mould. Subsequent treatment as described above for chitosan D1 resulted in a transparent film essentially consisting entirely of a mixture of deacetylated chitosan acetate salt and glycerol. Below, the material is referred to chitosan D2.

8. Preparation of a Fifth Example of a Solid Film-Type Chitosan (Chitosan D3)

In a further modified procedure, the glycerol containing solution of deacetylated chitosan was poured into a square-shaped mould which was covered with a two-layered film consisting of polyurethane/polyethylene (Platilon U073 PE, Epurex, Bomlitz/Germany), with the polyurethane side up and the polyethylene side fixed to the bottom of the mould. Subsequent treatment as described above for chitosan D1 resulted in a transparent film essentially consisting entirely of a mixture of deacetylated chitosan acetate salt and glycerol which was attached to the polyurethane/polyethylene support film. Below, the material is referred to as chitosan D3. Upon use, the polyethylene layer is removed. The remaining polyurethane layer is gas-permeable.

9. Preparation of a Sixth Example of a Solid Film-Type Chitosan (Chitosan D4)

In a slightly modified procedure to the preparation of chitosan film D2, 1% (w/w) glycerol was added to the filtered solution before pouring it into the square-shaped mould. Subsequent treatment as described above for chitosan D1 resulted in a transparent film essentially consisting entirely of a mixture of deacetylated chitosan acetate salt and glycerol. Below, the material is referred to chitosan D4.

10. Preparation of Two Examples of Chitosan with Higher DA (Chitosans E1 and F1)

Two further examples of chitosan were produced by the procedure leading to chitosan D1 with the only modification that in one case the hydrolysis step was shortened, leading to a DA of 4% (chitosan E1), and in the other case the hydrolysis step was entirely omitted, leading to a DA of 16% (chitosan F1).

11. Inhibition of *Escherichia coli* Growth on Agar

Figure 3:
FIG. 3 Illustrates the effect of a chitosan solution according to the invention on *Escherichia coli* cultivated on an agar plate after 12 hours of incubation.

An agar plate was coated with 200 µL of a suspension (appr. $10^8$ cells per ml) of the gram-positive bacterium *Escherichia coli*. A circular cavity was made in the plate and 100 µL of solution A1 was pipetted into the cavity. The plate was then incubated at 37° C. for 12 hours. The result of the experiment is shown in FIG. 3. A clear circular inhibition zone can be seen around the hole that contains the chitosan solution, indicating antibiotic activity of the chitosan solution against *Escherichia coli*.

12. Inhibition of *Staphylococcus carnosus* Growth on Agar

Figure 4:
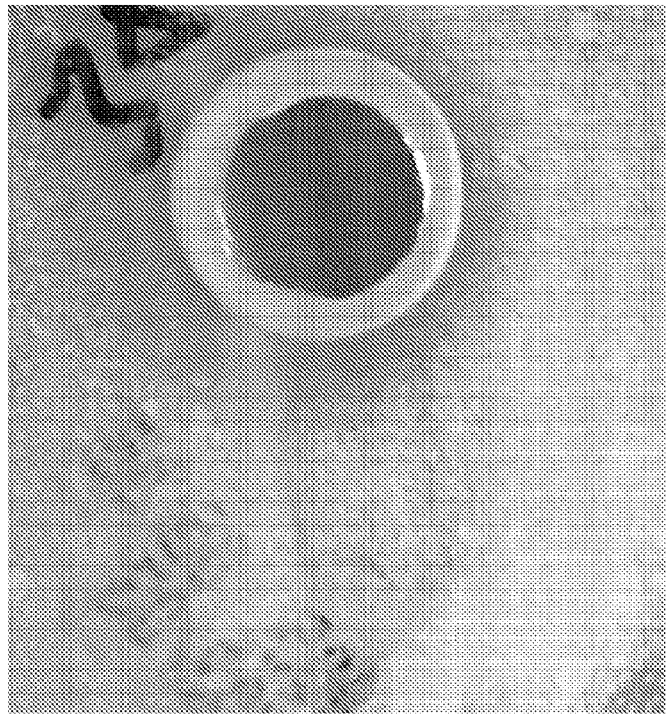
FIG. 4 Illustrates the effect of a chitosan solution according to the invention on *Staphylococcus carnosus* cultivated on an agar plate after 12 hours of incubation.

The above experiment was repeated with the gram-negative bacterium *Staphylococcus carnosus*. An agar plate was coated with 200 µL of a suspension (appr. $10^8$ cells per ml) of the bacterium and the solution A was pipetted into a cavity in the plate. The plate was then incubated at 37° C. for 12 hours. The result of the experiment is shown in FIG. 4. A clear circular inhibition zone can be seen around the hole that contains the chitosan solution, indicating antibiotic activity of the chitosan solution against *Staphylococcus carnosus*.

13. Inhibition of *Escherichia coli* Growth in Liquid Medium

Figure 5:
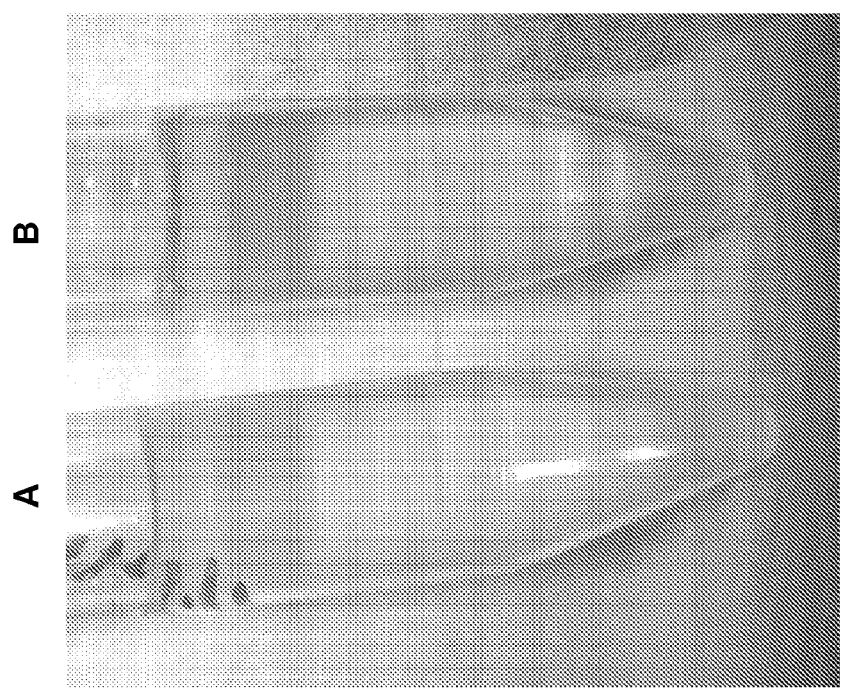
FIG. 5 Shows centrifuge tubes with samples of a Tryptic Soy Broth medium containing a chitosan preparation according to the invention (A) and free of chitosan (B)

In order to test the antibiotic activity of the chitosan preparation according to the invention, 5 mL of solution A1 was inoculated with 100 µL of overnight activated *E. coli* (optical cell density $OD_{500}=5$) at room temperature in a Tryptic Soy Broth liquid medium. The sample was filled in a centrifuge tube and is shown in FIG. 5 on the left (sample A). For comparison, 5 mL of TSB medium free of chitosan was inoculated with 100 µL of overnight activated *E. coli* (optical cell density $OD_{500}=5$). A centrifuge tube filled with the chitosan-fee sample is shown on the right in FIG. 5 (sample B). The inoculation was followed by 16 hours of incubation at room temperature under shaking.

Figure 6:
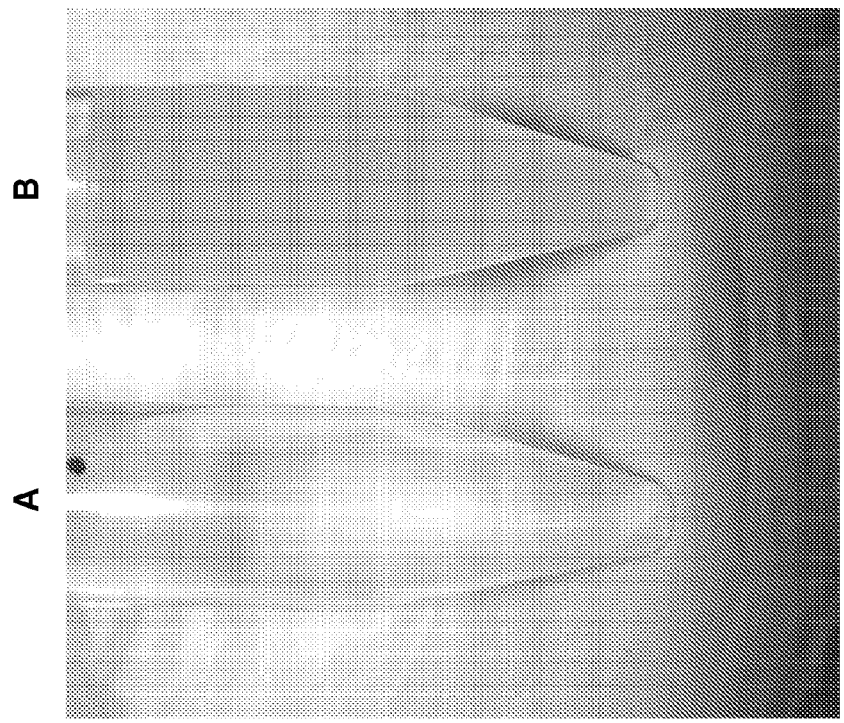
FIG. 6 Shows the samples of FIG. 3 after 16 hours of incubation following the inoculation with *Escherichia coli;*

The result of the experiment is shown in FIG. 6. In the medium without chitosan (sample B), a considerable increase in the turbidity of the solution was observed, indicating bacteria growth. In contrast, the chitosan containing solution (sample A) shows no discernable increase in the turbidity. The experiment thus indicates antibiotic activity of the chitosan solution against *Escherichia coli* in the Tryptic Soy Broth liquid medium.

14. Inhibition of *Escherichia coli* Growth in Liquid Medium

In another experiment to test the antibiotic activity of the chitosan preparation according to the invention, solution A1 was inoculated with *E. coli* K 12 (OD 0.2) in a lysogene broth medium for 15 hours at 37 deg C. under shaking. Solution A1 was added in different volumes to yield final chitosan concentrations as specified in Table 1.

The results of this experiment are summarized in Table 1

TABLE 1

|  | Chitosan concentration | | | | | Control |
|---|---|---|---|---|---|---|
|  | 0.75% | 0.3% | 0.1% | 0.03% | 0.01% | (no chitosan) |
| Observation | − | − | − | + | ++ | +++ |

− no growth;
+, ++, +++ growth in increasing order

The addition of 0.1% Chitosan to *E. coli* in exponential growth phase starting with an OD of 0.2 for 15 h at 37° C. and shaking (in *E. coli* optimal growth media) led to a clearing of the solution, the solution remained sterile for an additional observation period of 5 days (RT without shaking).

15. Efficacy of Antimicrobial Preservation

The efficacy of antimicrobial preservation was tested according to the norm as described in the Ph. Eur. $7^{th}$ Edition, Chapter 5.1.3, with solution A3. Two containers were each filled with 20 mL of solution A3 and inoculated with a suspension of either *Pseudomonas aeruginosa* ATCC 9027 or *Staphylococcus aureus* ATCC 6538 to give an inoculum of $10^5$ to $10^6$ microorganisms per mL. The suspension was mixed thoroughly to ensure homogeneous distribution. The inoculated product was maintained at 20° C. to 25° C. under protection from light. A 1 mL sample was removed from each container at zero hour and at the intervals specified in Table 2, and the number of viable microorganisms determined by plate count.

TABLE 2

|  | CFU per ml of sample | | | | |
|---|---|---|---|---|---|
| Bacteria | 0 h | 2 d | 7 d | 14 d | 28 d |
| *Pseudomonas aeruginosa* ATCC 9027 | $8.6 \times 10^5$ | <10 | <10 | <10 | <10 |
| *Staphylococus aureus* ATCC 6538 | $9.2 \times 10^5$ | <10 | <10 | <10 | <10 |

16. Antibiotic Activity of Chitosan Fibers

To demonstrate the antibiotic activity of chitosan fibers, a chitosan fiber was produced by extrusion of 50 mL of a solution of 4% chitosan in 2% acetic acid, mixed with an equal amount of N-methylpyrrolidone (NMP) through a needle of 50 mm in length and an inner diameter of 1.0 mm.

The needle was dipped into a coagulation bath containing a mixture of 2 L (liters) of NMP and 3 mL of 25% aqueous ammonia solution. After completion of the extrusion, the fiber was left in the coagulation bath over night. It was then washed twice in distilled water containing 0.1% by weight of a 25% aqueous ammonia solution for 2 hours, and then dried at room temperature.

*Staphylococcus carnosus* was cultured over night at room temperature in a Tryptic Soy Broth growth medium. Subsequently, 500 μL of the thus obtained bacteria suspension was used to coat a Mueller-Hinton Agar plate at pH 5.5. A chitosan fiber section of 4 centimeters in length and 0.2 millimeters in diameter was placed on the plate and incubated over night at 37° C.

Figure 7:
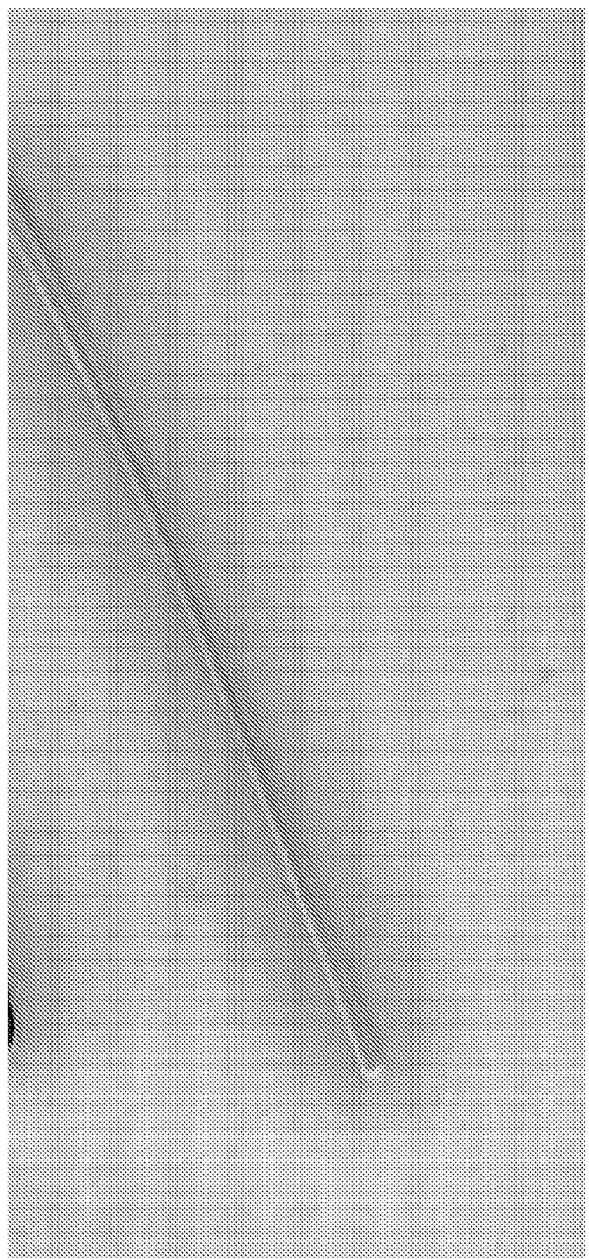
FIG. 7 Illustrates the effect of a chitosan fiber according to the invention on *Staphylococcus carnosus* cultivated on an agar plate after overnight incubation.

The result of the experiment is shown in FIG. 7. A clear inhibition zone around the chitosan fiber was observed, indication antibiotic activity of the fiber against *Staphylococcus carnosus*.

17. Treatment of a MRSA Infection

A 39 year old male patient who suffers from cerebro-orbito-facial arterio-venous malformation associated with recurrent severe bleeding from facial wounds was diagnosed with MRSA wound infection. He was treated by spraying chitosan solution A3 daily for 3 weeks onto the facial wounds. After the treatment MRSA viable microorganisms could not be detected anymore and no other microbial infection could be found at the site of the chitosan treatment.

18. Water Uptake of Chitosan C

Chitosan C, produced as described in the above example, was weighted, and then placed in distilled water for 15 min. The weight of the wet film was compared to the weight of the dry film, and the water uptake was determined to be 72% by weight.

19. Water Uptake of Chitosan D4

Chitosan D4, produced as described in the above example, was weighted, and then placed in distilled water for 60 min. The weight of the wet film was compared to the weight of the dry film, and the water uptake was determined to be 1217% by weight 7 days after film preparation, and 475% by weight 14 days after film preparation.

20. Dissolution of Chitosan

Controlled dissolution of chitosans B and C was tested in dissolution experiments using distilled water, 0.9% aqueous sodium chloride solution, and 0.5% acetic acid/acetate buffered solution, respectively. The pH of the solutions was adjusted to the values indicated in Table 2 using appropriate amounts of 1 N hydrochloric acid or sodium hydroxide solutions. Chitosans B and C were cut into rectangular samples having dry weights between 5 and 10 mg each. A gauze soaked with a 100-fold per volume excess of the respective solution to the dry weight of the film was applied to each sample film and the time for complete film dissolution was recorded.

TABLE 3

| pH of the dissolution mixture | Material B (distilled water) | Material B (0.9% aqueous sodium chloride) | Material C (0.9% aqueous sodium chloride) | Material C (0.5% acetic acid/acetate buffer) |
|---|---|---|---|---|
| 4.0 | n.a. | n.a. | n.d. | 0.5 h |
| 4.5 | n.a. | n.a. | n.d. | 0.5 h |
| 5.0 | n.a. | n.a. | n.d. | 2 h |
| 5.5 | 0.1 h | 0.5 h | n.d. | 4 h | n.a. = not analyzed
n.d. = no dissolution observed after 24 h

Figure 8:
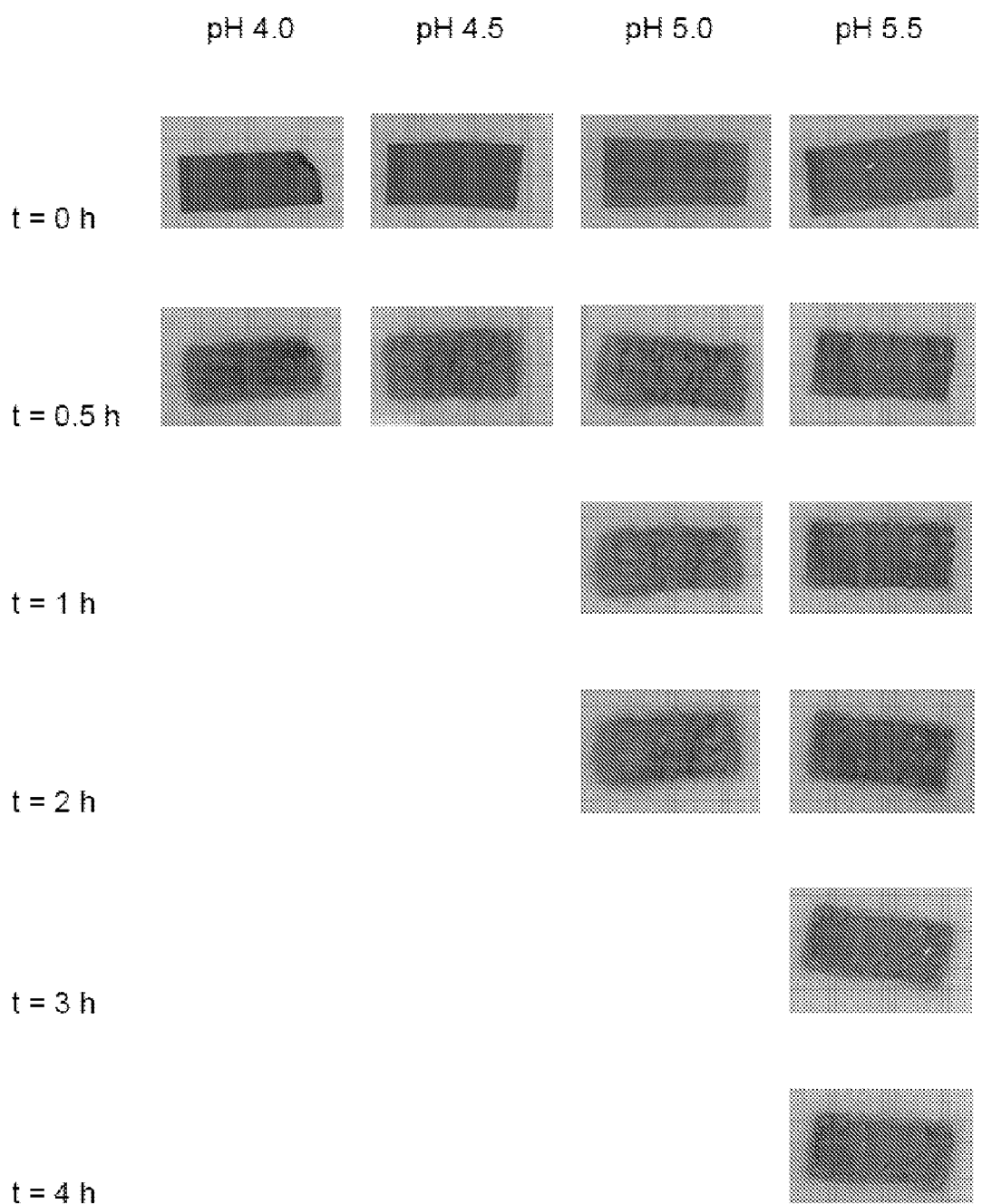
FIG. 8 illustrates the controlled dissolution of a chitosan according to the invention by applying gauze soaked with acetate buffered solution.

The controlled dissolution experiment with chitosan material C and a mixture of 0.5% acetic acid/sodium acetate (right column in Table 3), is illustrated in FIG. 8. The material has been stained by storage in 0.01% aqueous indigocarmine solution for 1 hour for better visualization. Complete dissolution was observed after 30 minutes at pH 4.0 and 4.5, after 2 hours at pH 5.0, and after 4 hours at pH 5.5, respectively.

21. In Situ Conversion of Water-Soluble Chitosan into Water-Insoluble Chitosan

Samples of solution A2 and chitosans D1, D2, D3 and D4 were left unsealed on air at room temperature and a humidity of 20-40%. Under these conditions, solution A2 was drying to a solid film within several hours. Complete dissolution in distilled water was analyzed at days 3, 7, and 14. Results are summarized in Table 4.

TABLE 4

| Chitosan | Day 3 | Day 7 | Day 14 |
|---|---|---|---|
| A2 | soluble | insoluble | insoluble |
| D1 | soluble | soluble | insoluble |
| D2 | soluble | insoluble | insoluble |
| D3 | soluble | insoluble | insoluble |
| D4 | soluble | insoluble | insoluble |

Similarly, conversion of the water-soluble into the water-insoluble form of dried solution A2 and chitosans D1, D2, D3 and D4 was observed after application of the wound dressing on human skin. In the case of D3, the chitosan was applied to the skin with its chitosan side. Conversion of the water-soluble into the water-insoluble form dried solution A2 and chitosans D1, D2, D3 and D4 was also observed after alkaline treatment or storage in an alkaline atmosphere.

22. Dissolution of Chitosan with Detachment Solvent

Chitosans D1, E1 and F1 were dissolved by storage in a 2% acetic acid/acetate buffered solution. The pH of the storing solutions was adjusted to the values indicated in Table 5 using appropriate amounts of 10% sodium hydroxide solutions. Films D1, E1 and F1 made from chitosans with different degrees of acetylation (DA) were left on air for 14 days for conversion into the water-insoluble form, cut into rectangular samples of 1×1 cm² size and stored in approximately 10 mL of the respective solution, and the time for complete film dissolution was recorded.

TABLE 5

| pH | DA = 16% | DA = 4% | DA = 1.5% |
|---|---|---|---|
| | Time for complete dissolution (min) | | |
| 4.0 | 5 | 10 | 1 |
| 4.5 | 15 | 15 | 2 |
| 5.0 | 30 | 15 | 15 |
| 5.5 | 60 | 60 | 30 |
| 6.0 | 60 | overnight | overnight |

Figure 9A:
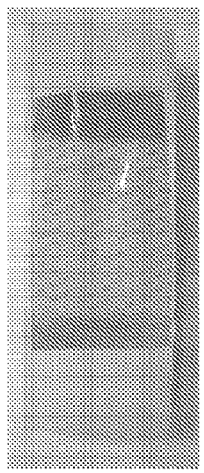
FIG. 9 shows a tissue dressing comprising a chitosan according to the invention before (9a), during (9b), and after (9c) the application of the detachment solvent.
Figure 9B:
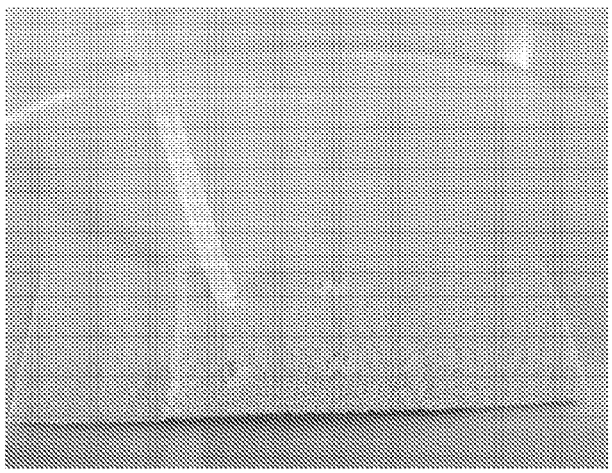
Figure 9C:
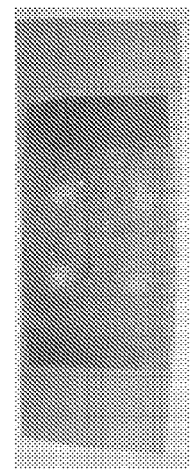

In another dissolution experiment, a film C (3×1 cm²) was fixed on the inside of a commercial perforated band-aid (5×2 cm) which was then fixed on a Petri dish. An acetic acid/acetate buffered solution (pH 5.5) was added dropwise through the perforations of the band-aid causing the wound dressing material film to dissolve. The side of the tissue dressing comprising the film is shown in FIG. 9a before and in FIG. 9c after application of the solution. The application of the solution to the band-aid side of the wound dressing is shown in FIG. 9b.

23. Analysis of Non-Soluble and Soluble Fractions of Low-DA Chitosan 0.1 g samples of chitosan with a DA of 1.5%, prepared as described in Example 2, were placed each in 10 ml of phosphate-buffered solution and kept at room temperature under gentle shaking at pH 7.4. At the time points given in Table X, the mixture was filtered, and the non-soluble chitosan remaining in the filter was thoroughly washed and finally dried. The amount of the non-soluble chitosan was determined gravimetrically on a laboratory scale. The results are summarized in Table 6:

TABLE 6

| | Time of storage in PBS | | | | |
|---|---|---|---|---|---|
| | 1 hour | 8 hours | 1 day | 3 days | 10 days |
| non-soluble chitosan fraction (%) | 95.5 | 93.5 | 84 | 85 | 84.5 |
| soluble chitosan fraction (%) | 4.5 | 6.5 | 16 | 15 | 15.5 |

24. Cell Viability on Low-DA Chitosan

Figure 14:
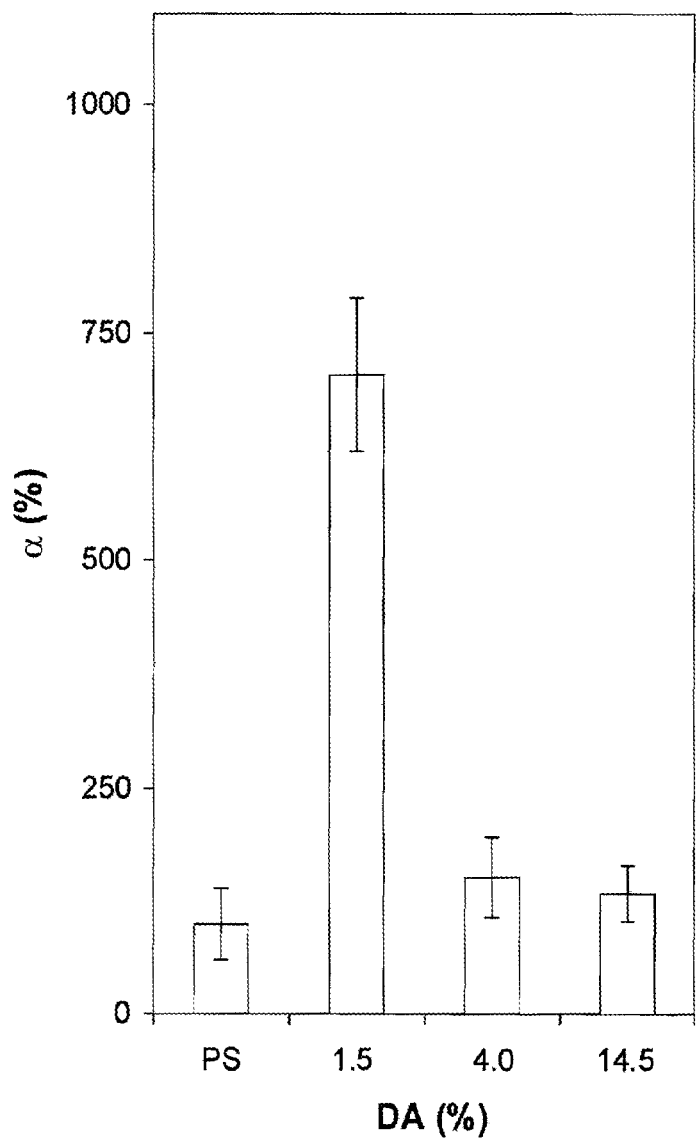
FIG. 14 illustrates the cell viability of keratinocytes on chitosan materials of various degrees of acetylation, relative to tissue culture polystyrene controls (PS=100%)

Chitosan films having DAs of 1.5, 4.0, and 14.5%, respectively, were placed in 24-well cell culture plates, and human HaCaT keratinocytes were seeded at a density of $5 \times 10^4$ cells per $cm^2$ and cultured for 2 days. Cell viability was determined using the MTS assay (Promega). After 4 h of MTS incubation with the cells, the light absorbance at 490 nm was measured by an ELISA plate reader and subtracted from that of the controls (without cells) to yield the corrected absorbance. Five samples of each DA were studied. FIG. 14 shows the relative light absorbencies α at 490 nm (PS=100%) for the three samples and a control using polystyrene (PS).

25. Cell Growth on Chitosans of Different DA

Figure 15:
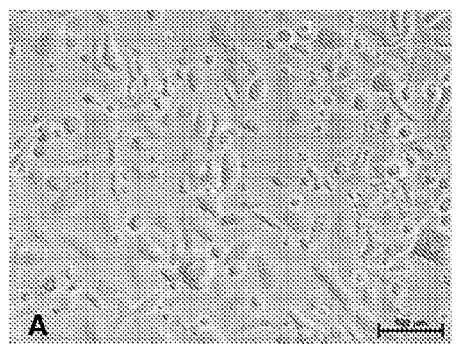
FIG. 15 shows microscopic images of human keratinocytes grown on chitosan materials of various degrees of acetylation (A: 1.5%; B: 14.5%).
Figure 15:
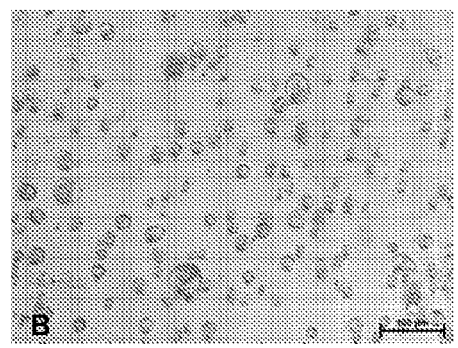

Human keratinocytes ($5 \times 10^4$ cells per well) were grown in a 24 well plate for 2 days at 37° C. on chitosan films having DAs of 1.5 and 14.5%, respectively. For the tests cells were isolated from human skin and grown until sub-confluency was reached. After 24 h the medium (Keratinocyte medium with Supplement Mix, Promocell) was changed in order to remove non-adherent cells. FIG. 15 gives representative examples of cells grown on chitosan films after 1 day of incubation.

Figure 10:
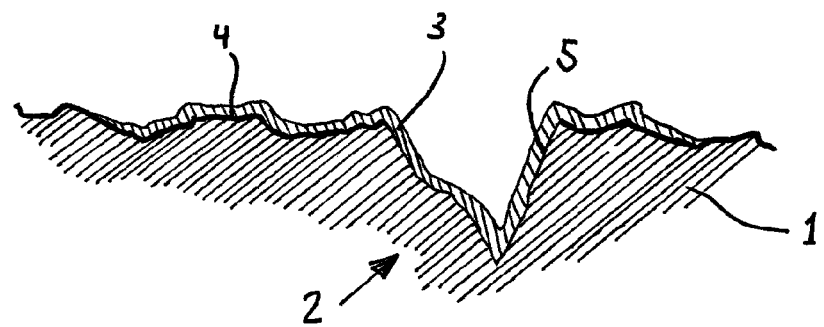
FIG. 10 schematically illustrates a wound to which a liquid chitosan containing composition according to the inventions has been applied.

In FIG. 10, schematically a tissue 1 comprising a wound 2 is shown. For better illustration, FIGS. 5 to 8 are not drawn to scale. The liquid chitosan containing composition according to the invention has been applied to the tissue 2 and the constituent water has been allowed to evaporate, leaving behind a film 3 that dresses the tissue 2 including the wound 3. In general, the film 3 is about 10 to 20 μm thick. Advantageously, the film 3 tightly snuggles to the tissue surface 4, including the wound surface 5.

Figure 11:
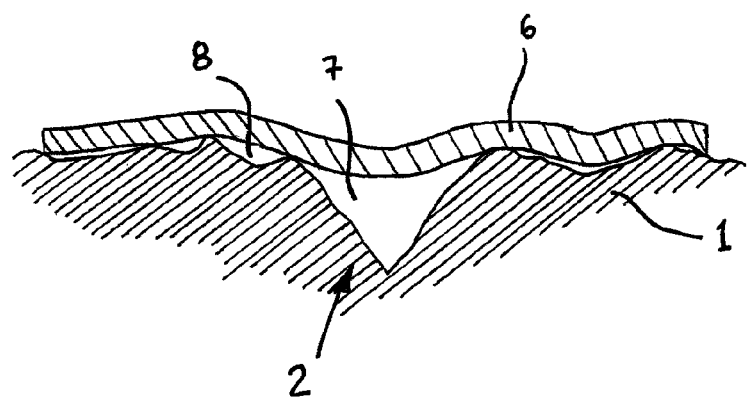
FIG. 11 schematically illustrates a wound to which a solid chitosan material according to the inventions has been applied.

FIG. 11 schematically shows a chitosan in the form of a solid film 6 that is applied to a tissue 1, comprising a wound 2. The solid film is about 80 μm thick. Cavities 7, 8 between the tissue 1 and the chitosan 6 may be filled with water or exudative fluid.

Figure 12:
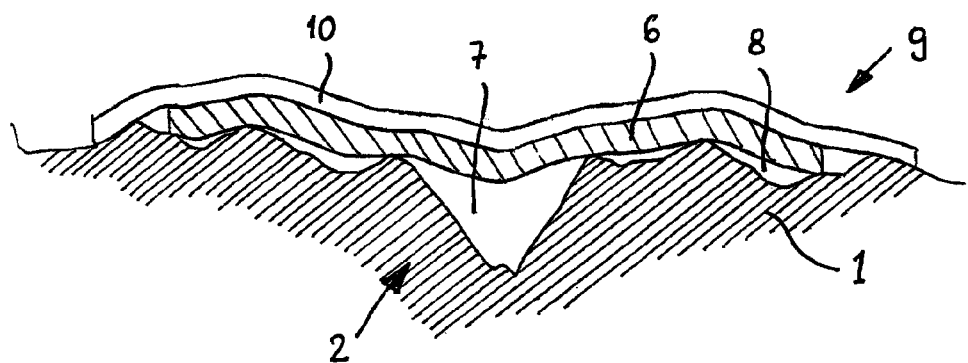
FIG. 12 schematically illustrates a wound to which a non-perforated wound dressing according to the invention has been applied.
Figure 13:
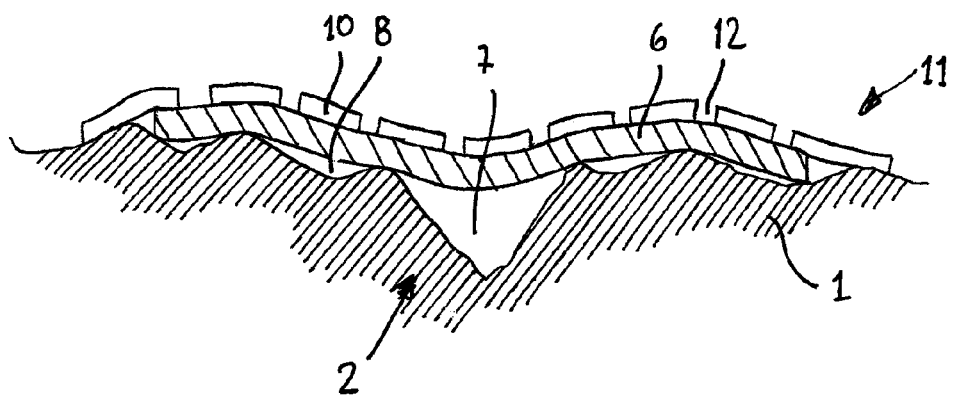
FIG. 13 schematically illustrates a wound to which a perforated wound dressing according to the invention has been applied.

In FIG. 12, a tissue dressing 9 comprising a chitosan film 6 of FIG. 11 as a first layer and a silicon film 10 as a second layer is applied to a tissue 1, comprising a wound 2. The silicon film 10 is about 50 μm tick. Again, cavities 7, 8 between the tissue 1 and the tissue dressing material 6 may be filled with water or exudative fluid. Finally, FIG. 13 shows a tissue dressing 11 applied to a tissue 1 comprising a wound 2, the tissue dressing 11 differing from that 9 of FIG. 12 in that the silicon film 10 is perforated to allow an exchange of air between the tissue 1 and the surrounding though the wound dressing material 6. The perforations have a diameter if between 50 and 100 μm.

The features described in the above description, claims and figures can be relevant to the invention in any combination. The reference numerals in the claims have merely been introduced to facilitate reading of the claims and are by no means meant to be limiting.

What is claimed is:

1. A method for stimulating epithelial growth of a tissue, wherein the tissue comprises cuts, abrasions, burns, razor burn, irritated skin, malar rash, wounds caused by viruses, insect bites and tissues affected by acne, comprising: administering to the tissue an effective amount of a spray comprising chitosan with a degree of acetylation of greater than 0% but equal to or less than 2.5%.

2. The method according to claim 1, wherein the chitosan is provided as liquid composition.

3. The method according to claim 2, wherein the chitosan is in aqueous solution.

4. The method according to claim 3, wherein the chitosan is in aqueous solution in a concentration of less than 15% by weight.

5. The method according to claim 2, wherein the chitosan-containing composition comprises an organic acid selected from the group of monobasic or multibasic organic acids having 2 to 12 carbon atoms and a first pKa value between 1 and 5.

6. The method according to claim 2, wherein the chitosan-containing composition is free of organic solvents.

7. The method according to claim 2, wherein the chitosan-containing composition allows for formation of a film after administration to the tissue and wherein the film is less than 1 mm thick.

8. The method according to claim 1, wherein the chitosan is native chitosan.

9. The method according to claim 1, wherein the degree of acetylation of the chitosan is less than 2%.

10. The method according to claim 1, wherein the chitosan is preparable by a method that involves at least two deacetylation steps.

11. The method according to claim 1, wherein a fraction of more than 10% of the chitosan is present in a form that is insoluble at a pH of 6.5 or greater.

12. The method according to claim 2, wherein the chitosan-containing composition is provided as a kit in combination with a detachment solution.

13. The method according to claim 3, wherein the chitosan is in aqueous solution in a concentration of less than 10% by weight.

14. The method according to claim 3, wherein the chitosan is in aqueous solution in a concentration of less than 7.5% by weight.

15. The method according to claim 3, wherein the chitosan is in aqueous solution in a concentration of less than 5% by weight.

16. The method according to claim 1, wherein the chitosan is removed with an acidic detachment solvent.

17. The method according to claim 1, wherein the chitosan is removed with an aqueous detachment solvent.

* * * * *